United States Patent [19]

Hasegawa et al.

[11] Patent Number: 5,700,918
[45] Date of Patent: Dec. 23, 1997

[54] MORANOLINE DERIVATIVE

[75] Inventors: Akira Hasegawa; Makato Kiso, both of Gifu; Yoshiaki Yoshikuni, Uji, all of Japan

[73] Assignee: Nippon Shinyaku Co., Ltd., Japan

[21] Appl. No.: 718,421

[22] PCT Filed: Mar. 30, 1995

[86] PCT No.: PCT/JP95/00610

§ 371 Date: Sep. 20, 1996

§ 102(e) Date: Sep. 20, 1996

[87] PCT Pub. No.: WO95/26970

PCT Pub. Date: Oct. 12, 1995

[30] Foreign Application Priority Data

Apr. 1, 1994 [JP] Japan .................. HEI-6/065300

[51] Int. Cl.$^6$ .................. C07H 5/04
[52] U.S. Cl. .................. 536/18.7; 536/17.2; 536/4.1; 536/6.2; 514/27
[58] Field of Search .................. 536/17.2, 18.7, 536/4.1, 6.2; 514/27

[56] References Cited

U.S. PATENT DOCUMENTS 5,498,604 3/1996 Hasegawa et al. .................. 514/27

OTHER PUBLICATIONS

Makoto et al., Synthetic Studies on Gialo-glycoconjugates 45:Synthesis of 1–Deoxynojinimycin–Containing Oligosacchinides Related to the Cancer–Associated Sialyl–Lewis a Antigen Recognized by LEC–CAMS (Selectins), J. Canbohydrate Chem. 1993, 12, 673–677.

Makoto et al, Synthetic Studies on Sialylglycoconjugates. Part 62. Systematic Synthesis of N–Methyl–1–Deoxyjinimycin–Containing, Lex, Lea, Sialyl–Lex and Sialyl–Lea Epitopes Recognized by Selectins. Bioorg. Med. Chem. 1994, 2, 1295–1308.

*Primary Examiner*—John Kight
*Assistant Examiner*—Friedrich N. Burnett
*Attorney, Agent, or Firm*—Graham & James LLP

[57] ABSTRACT

The present invention has for its object to provide a trisaccharide Lewis sugar-chain epitope derivative of the following structural formula, which is of value as a medicine and has a novel structure containing moranoline.

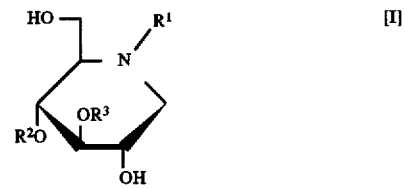

wherein $R^1$ represents hydrogen or lower alkyl; $R^2$ and $R^3$ are dissimilar and each represents galactopyranosyl or fucopyranosyl, which is substituted by hydroxysulfonyl or a metal salt thereof. The compounds of the invention have cell adhesion-inhibitory activity and is useful for the prevention and treatment of inflammation, inflammation-associated thrombosis, rheumatism, immune diseases, viral infections, and cancer.

4 Claims, No Drawings

MORANOLINE DERIVATIVE

TECHNICAL FIELD

The present invention relates to a novel moranoline derivative which is of use in the medicinal field, for example as an antiinflammatory agent or an antiviral agent.

BACKGROUND TECHNOLOGY

The sugar chains of sialic acid-containing glycolipids and glycoproteins have receptor functions for hormones, bacterial toxins, viruses, etc. and are closely associated with the fundamental and dynamic vital phenomena such as the recognition, differentiation, proliferation, adhesion, cancerization, immunity, and senescence of cells, thus being current subjects of interest.

For example, their application as antiviral agents has been reported in JP Kokai S63-139193 and JP Kokai H3-251593 and as immunomodulators in JP Kokai S61-243074 and JP Kokai S62-209094. Furthermore, their application to cancer diagnosis and therapy has been described in JP Kokai S61-63700.

These sialic acid derivatives exist as traces in the natural kingdom and, therefore, it has been considerably difficult to isolate such compounds as pure singular entities from biological materials. For this reason, explorations into sialic acid derivatives for exploitation as medicines constitute a new domain of research with good promises of clinical application.

The inventors of the present invention explored into a varies of sugar-chain epitope derivatives, discovered novel sialyl Lewis sugar-chain epitope derivatives including moranoline having medicinally meritorious pharmacologic actions, and perfected the invention disclosed in PCT/JP 93/00106 (WO 93/15098).

The tetrasaccharide sialyl Lewis epitope sugar-chain derivative according to said PCT/JP 93/00106 was found to be a substance possessing meritorious pharmacological features but because its synthesis required many steps and complicated procedures, the compounds could hardly be synthesized economically and efficiently so that the technology was not fully satisfactory for production on a commercial scale.

According to recent studies, like sialyl tetrasaccharide Lewis sugar-chain epitope derivatives, non-sialic acid-containing trisaccharide hydroxysulfonyl Lewis sugar-chain epitope derivatives also have antagonistic activity against selectins which are associated with cell adhesion (Glycobiology, Vol. 3, no. 6, pp. 633–639, 1993).

DISCLOSURE OF THE INVENTION

The present invention has for its object to provide a trisaccharide hydroxysulfonyl Lewis epitope moranoline derivative which is structurally simpler than the known sugar-chain epitope derivatives and can be easily produced.

The inventors of the present invention did further research and found that a compound of general formula [I], which is a moranoline derivative available upon substitution of a sulfate group for the sialic acid residue of the compounds disclosed in said PCT/JP93/00106 meets the above object. They have accordingly perfected the present invention.

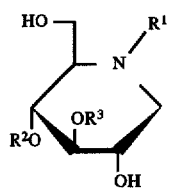

wherein $R^1$ represents hydrogen or lower alkyl; $R^2$ and $R^3$ are dissimilar and each represents galactopyranosyl which may be optionally substituted by hydroxysulfonyl or a metal salt thereof, or fucopyranosyl.

Compared with the process required for production of the compounds of said PCT/JP93/00106, the production process for the compounds of the present invention employs hydroxysulfonyl in lieu of sialyl and, as such, represents marked improvements in process parameters, time, and other economic factors.

The compounds of general formula [I] according to the present invention are not only novel compounds not heretofore documented but are substances possessing very meritorious pharmacologic actions as described hereinafter.

Referring, now, to general formula [I], the lower alkyl $R^1$ is preferably a straight-chain or branched-chain alkyl group of 1–7 carbon atoms, such as methyl, ethyl, n-propyl, isopropyl, n-butyl, isobutyl, t-butyl, n-pentyl, isopentyl, n-hexyl, isohexyl, n-heptyl, and isoheptyl.

The preferred alkali metal salt of the hydroxysulfonyl residue in the compounds of the present invention includes salts with lithium, sodium, and potassium, and the preferred alkaline earth metal salt includes salts with magnesium, calcium, and barium.

The compounds of the present invention includes the following species in addition to those described in the examples which appear hereinafter. It should be understood that all of these compounds constitute a merely illustrative and not exhaustive listing of the compounds of the invention.

O-(3-O-sulfo-β-D-galactopyranosyl)-(1→4)-O-[(α-L-fucopyranosyl)-(1→3)]-1,5-imino-D-glucitol sodium salt O-(3-O-sulfo-β-D-galactopyranosyl)-(1→4)-O-[(α-L-fucopyranosyl)-(1→3)]-1,5-imino-N-ethyl-D-glucitol sodium salt O-(3-O-sulfo-β-D-galactopyranosyl)-(1→4)-O-[(α-L-fucopyranosyl)-(1→3)]-1,5-imino-N-propyl-D-glucitol sodium salt O-(3-O-sulfo-β-D-galactopyranosyl)-(1→4)-O-[(α-L-fucopyranosyl)-(1→3)]-1,5-imino-N-butyl-D-glucitol sodium salt O-(3-O-sulfo-β-D-galactopyranosyl)-(1→4)-O-[(α-L-fucopyranosyl)-(1→3)]-1,5-imino-N-pentyl-D-glucitol sodium salt O-(3-O-sulfo-β-D-galactopyranosyl)-(1→4)-O-[(α-L-fucopyranosyl)-(1→3)]-1,5-imino-N-hexyl-D-glucitol sodium salt O-(3-O-sulfo-β-D-galactopyranosyl)-(1→3)-O-[(α-L-fucopyranosyl)-(1→4)]-1,5-imino-D-glucitol sodium salt O-(3-O-sulfo-β-D-galactopyranosyl)-(1→3)-O-[(α-L-fucopyranosyl)-(1→4)]-1,5-imino-N-ethyl-D-glucitol sodium salt O-(3-O-sulfo-β-D-galactopyranosyl)-(1→3)-O-[(α-L-fucopyranosyl)-(1→4)]-1,5-imino-N-propyl-D-glucitol sodium salt O-(3-O-sulfo-β-D-galactopyranosyl)-(1→3)-O-[(α-L-fucopyranosyl)-(1→4)]-1,5-imino-N-butyl-D-glucitol sodium salt O-(3-O-sulfo-β-D-galactopyranosyl)-(1→3)-O-[(α-L-fucopyranosyl)-(1→4)]-1,5-imino-N-pentyl-D-glucitol sodium salt O-(3-O-sulfo-β-D-galactopyranosyl)-(1→3)-O-[(α-L-fucopyranosyl)-(1→4)]-1,5-imino-N-hexyl-D-glucitol sodium salt The compounds of the present invention can be produced in accordance with the disclosure in the examples which appear hereinafter.

The compounds possessing cell adhesion-inhibitory activity inhibit adhesion of leukocytes or cancer cells to endothelial cells by competitive antagonism against selectin occurring in the endothelial cells and, therefore, it is certainly useful for the prophylaxis and therapy of inflammation and associated thrombosis, rheumatism, infection, immune disease, AIDS, and cancer.

Therefore, the compounds of the present invention are of value as an antiviral agent, an antiinflammatory agent, an antithrombotic agent, an anti-rheumatic, an anti-ineffective agent, an anti-AIDS agent, or a prophylactic and therapeutic agent for immune disease and cancer.

In using the compounds of the present invention as a medicine, the compounds can be administered to animals inclusive of man, either as they are or in the form of a pharmaceutical composition containing 0.1%–99.5%, preferably 0.5%–90%, of the compound and the balance of a medicinally acceptable nontoxic, inert carrier.

The carrier may be one or more kinds of solid, semisolid, or liquid diluents, fillers, and other formulation auxiliaries. The pharmaceutical composition is preferably administered in unit dosage forms. The pharmaceutical composition of the present invention can be administered, parenterally, locally (e.g. transdermally), or rectally. Of course, a dosage form suited for each route of administration should be selected. A particularly preferred route is parenteral.

The dosage as an antiviral agent is preferably tailored to the patient factors such as age and body weight, route of administration, and nature and severity of illness, among other factors. Usually, in adults, 100 mg–3 g/day/patient, preferably 500 mg–1 g/day/patient, as the active compound of the invention is generally recommended. A lower dosage may be sufficient in some cases, while a higher dosage may be necessary in other cases. Preferably the above dosage is administered in at most 3 divided doses.

The following examples and test examples are further illustrative of the present invention. The optical rotation values shown are invariably the measured values at 25° C.

[EXAMPLE 1]

Process For Production of a Lewis X Moranoline Derivative

Synthesis of O-(3-O-sulfo-β-D-galactopyranosyl)-(1→4)-O-[(α-L-fucopyranosyl)-(1→3)]-1,5-imino-N-methyl-D-glucitol sodium salt

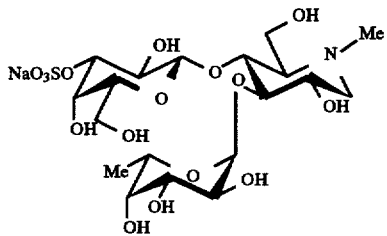

(1) Synthesis of methyl 4,6-O-benzylidene-3-O-levuloyl-1-thio-β-D-galactopyranoside In dichloromethane (10 ml)-pyridine (10 ml) was dissolved methyl 4,6-O-benzylidene-1-thio-β-D-galactopyranoside (100 mg) followed by addition of 4-dimethylaminopyridine (41 mg, 1 eq.). After the mixture was cooled to −50° C., a solution of levuloyl chloride (179 mg, 2.5 eq.) in dichloromethane (5 ml) was added dropwise and the mixture was stirred at −50° C. for 30 minutes. After the completion of reaction was confirmed by TLC, the reaction mixture was extracted with dichloromethane and washed with 2N hydrochloric acid and water. The organic layer was dehydrated over anhydrous sodium sulfate and filtered. The filtrate and washings were pooled and concentrated under reduced pressure. The residue was subjected to column chromatography (Wakogel C-200, eluent: ethyl acetate-hexane=1:1) to provide the title compound (1; 85 mg, 64%).

Optical rotation $[\alpha]_D$+40.07° (c=1.682, dichloromethane)
Elemental analysis for $C_{19}H_{24}O_7S$ [mol. wt. 396.46] Calcd. (%): C, 57.56; H, 6.10; N, 0.00 Found (%): C, 57.32; H, 6.02; N, 0.00

(2) Synthesis of methyl 2-O-benzoyl-4,6-O-benzylidene-3-O-levuloyl-1-thio-β-D-galactopyranoside The above compound (1; 104 mg) was dissolved in pyridine (10 ml) followed by addition of benzoyl chloride (0.08 ml, 2.5 eq.) and the mixture was stirred at room temperature overnight. After the completion of reaction was confirmed by TLC, the reaction mixture was extracted with dichloromethane and washed with 2N hydrochloric acid and water. The organic layer was dehydrated over anhydrous sodium sulfate and filtered. The filtrate and washings were pooled and concentrated under reduced pressure. The residue was subjected to column chromatography (Wakogel C-200, eluent: ethyl acetate-hexane=1:2) to provide the title compound (2; 111 mg, 85%).

Optical rotation $[\alpha]_D$+55.93° (c=1,230, dichloromethane)
Elemental analysis for $C_{26}H_{28}O_8S$ [mol. wt. 500.57] Calcd. (%): C, 62.39; H, 5.64; N, 0.00 Found (%): C, 62.16; H, 5.55; N, 0.00

(3) Synthesis of O-(2-O-benzoyl-4,6-O-benzylidene-3-O-levuloyl-β-D-galactopyranosyl)-(1→4)-O-[(2,3,4-tri-O-benzyl-α-L-fucopyranosyl)-(1→3)]-2-O-acetyl-6-O-benzyl-N-benzyloxycarbonyl-1,5-dideoxy-1,5-imino-D-glucitol The above compound (2; 154 mg) and (2,3,4-tri-O-benzyl-α-L-fucopyranosyl)-(1→3)-2-O-acetyl-6-O-benzyl-N-benzyloxycarbonyl-1,5-dideoxy-1,5-imino-D-glucitol (182 mg, 2 eq) were dissolved in dichloromethane (5 ml). To this solution was added the desiccant molecular sieves 4A (300 mg) and the mixture was stirred at room temperature overnight. After cooling to 0° C., N-iodosuccinimide (164 mg, 4 eq) and trimethylsilyl trifluoromethanesulfonate (14 μl, 0.4 eq) were added and the mixture was stirred at 0° C.–room temperature overnight. After the completion of reaction was confirmed by TLC, the molecular sieves were filtered off and the filtrate was extracted with dichloromethane. The extract was then washed serially with sodium carbonate solution, sodium thiosulfate solution, and water. The organic layer was dehydrated over anhydrous sodium sulfate and filtered and the filtrate and washings were pooled and concentrated under reduced pressure. The residue was subjected to column chromatography (Wakogel C-200, eluent: ethyl acetate-hexane=1:2) to provide the title compound (3; 164 mg, 70%).

Optical rotation $[\alpha]_D$−30.28° (c=1.334, dichloromethane)
Elemental analysis for $C_{75}H_{79}NO_{19}$ [mol. wt. 1298.445] Calcd. (%): C, 69.38; H, 6.13; N, 1.08 Found (%): C, 69.13; H, 6.06; N, 1.03

(4) Synthesis of O-(2-O-benzoyl-3-O-levuloyl-β-D-galactopyranosyl)-(1→4)-O-[(2,3,4-tri-O-benzyl-α-L-fucopyranosyl)-(1→3)]-2-O-acetyl-6-O-benzyl-N-benzyloxycarbonyl-1,5-dideoxy-1,5-imino-D-glucitol In 80% acetic acid-water (10 ml) was dissolved the above compound (3; 164 mg) and the solution was stirred at 45° C. overnight. After the completion of reaction was confirmed by TLC, the reaction mixture was concentrated under reduced pressure and the residue was subjected to column chromatography (Wakogel C-200; eluent: ethyl acetate-hexane, 3:1) to provide the title compound (4; 136 mg, 89%).

Optical rotation $[\alpha]_D$ -39.13° (c=0.976, dichloromethane)

Elemental analysis for $C_{68}H_{75}NO_{19}$ [mol. wt. 1210.337] Calcd. (%): C, 67.48; H, 6.25; N, 1.16 Found (%): C, 67.36; H, 6.93; N, 0.94

(5) Synthesis of O-(2,4,6-tri-O-benzoyl-3-O-levuloyl-β-D-galactopyranosyl)-(1→4)-O-[(2,3,4-tri-O-benzyl-α-L-fucopyranosyl)-(1→3)]-2-O-acetyl-6-O-benzyl-N-benzyloxycarbonyl-1,5-dideoxy-1,5-imino-D-glucitol The above compound (4; 48 mg) was dissolved in pyridine (5 ml) followed by addition of benzoyl chloride (18 μl, 4 eq) and the mixture was stirred at room temperature overnight. After the completion of reaction was confirmed by TLC, the reaction mixture was extracted with dichloromethane and washed with 2N hydrochloric acid and water. The organic layer was dehydrated over anhydrous sodium sulfate and filtered. The filtrate and washings were pooled and concentrated under reduced pressure. The residue was subjected to column chromatography (Wakogel C-200, eluent: ethyl acetate-hexane=2:3) to provide the title compound (5; 48 mg, 86%).

Optical rotation $[\alpha]_D$ -36.76° (c=0.952, dichloromethane)

Elemental analysis for $C_{82}H_{83}NO_{21}$ [mol. wt. 1418.553] Calcd. (%): C, 69.43; H, 5.90; N, 0.99 Found (%): C, 69.13; H, 5.85; N, 0.95

(6) Synthesis of O-(2,4,6-tri-O-benzoyl-β-D-galactopyranosyl)-(1→4)-O-[(2,3,4-tri-O-benzyl-α-L-fucopyranosyl)-(1→3)]-2-O-acetyl-6-O-benzyl-N-benzyloxycarbonyl-1,5-dideoxy-1,5-imino-D-glucitol The above compound (5; 131 mg) was dissolved in ethanol (20 ml) followed by addition of hydrazine acetate (10 mg, 1.2 eq) and the mixture was stirred at room temperature overnight. After the completion of reaction was confirmed by TLC, the reaction mixture was concentrated and the residue was subjected to column chromatography (Wakogel C-200, eluent: dichloromethane-methanol=125:1) to provide the title compound (6; 122 mg, quantitative).

Optical rotation $[\alpha]_D$ -50.16° (c=2.388, dichloromethane)

Elemental analysis for $C_{77}H_{77}NO_{19}$ [mol. wt. 1320.45] Calcd. (%): C, 70.04; H, 5.88; N, 1.06 Found (%): C, 69.88; H, 5.75; N, 1.01

(7) Synthesis of O-(2,4,6-tri-O-benzoyl-3-O-sulfo-β-D-galactopyranosyl)-(1→4)-O-[(2,3,4-tri-O-benzyl-α-L-fucopyranosyl)-(1→3)]-2-O-acetyl-6-O-benzyl-N-benzyloxycarbonyl-1,5-dideoxy-1,5-imino-D-glucitol The above compound (6; 119 mg) was dissolved in N,N-dimethylformamide (0.5 ml) followed by addition of pyridine-sulfur trioxide complex (115 mg, 8 eq) and the mixture was stirred at room temperature overnight. After the completion of reaction was confirmed by TLC, methanol (1 ml) was added at 0° C. and the mixture was stirred for 30 minutes. This reaction mixture was concentrated under reduced pressure and the residue was subjected to column chromatography (Wakogel C-200, eluent: dichloromethane-methanol=15:1) to provide the title compound (7; 121 mg, 96%).

Optical rotation $[\alpha]_D$ -16.55° (c=2.416, dichloromethane)

Elemental analysis for $C_{77}H_{77}NO_{22}S$ [mol. wt. 1400.51] Calcd. (%): C, 66.04; H, 5.54; N, 1.00 Found (%): C, 65.89; H, 5.54; N, 0.83

(8) Synthesis of O-(2,4,6-tri-O-benzoyl-3-O-sulfo-β-D-galactopyranosyl)-(1→4)-O-[(α-L-fucopyranosyl)-(1→3)]-2-O-acetyl-1,5-dideoxy-1,5-imino-N-methyl-D-glucitol sodium salt The above compound (7; 114 mg) was treated with the ion exchange resin Dowex-$Na^+$ and dissolved in methanol (5 ml). Then, formalin (0.5 ml) and palladium chloride (300 mg) subjected to catalytic hydrogenation and washed with methanol beforehand were added. The mixture was subjected to catalytic hydrogenation reaction at room temperature with reaction was confirmed by TLC, the palladium was filtered off and washed with methanol. The filtrate and washings were pooled and concentrated under reduced pressure and the residue was subjected to column chromatography (Wakogel C-200, eluent: dichloromethane-methanol= 10:1) to provide the title compound (8; 62 mg, 83%).

Optical rotation $[\alpha]_D$ -30.49° (c=0.892, methanol)

Elemental analysis for $C_{42}H_{48}NO_{20}SNa$ [mol. wt. 941.89] Calcd. (%): C, 53.56; H, 5.14; N, 1.49 Found (%): C, 53.46; H, 4.97; N, 1.44

(9) Synthesis of O-(3-O-sulfo-β-D-galactopyranosyl)-(1→4)-O-[(α-L-fucopyranosyl)-(1→3)]-1,5-dideoxy-1,5-imino-N-methyl-D-glucitol sodium salt The above compound (8; 49 mg) was dissolved in methanol (50 ml) followed by addition of sodium methoxide until the pH became 12. The mixture was then stirred at room temperature over night. After the completion of reaction was confirmed by TLC, the reaction mixture was concentrated under reduced pressure and the residue was subjected to gel filtration (Sephadex LH-20, eluent: methanol-water=1:1) to provide the title compound (9; 30 mg, quantitative).

Optical rotation $[\alpha]_D$ -47.21° (c=0.466, methanol-water= 1:1)

Elemental analysis for $C_{19}H_{34}NO_{16}SNa$ [mol. wt. 587.53 ] Calcd. (%): C, 38.84; H, 5.83; N, 2.38 Found (%): C, 38.56; H, 5.72; N, 2.16

[EXAMPLE 2]

Process For Producing a Lewis A Sugar-Chain Derivative

Synthesis of O-(3-O-sulfo-β-D-galactopyranosyl)-(1→3) -O-[(α-L-fucopyranosyl)-(1→4)]-1,5-imino-N-methyl-D-glucitol sodium salt

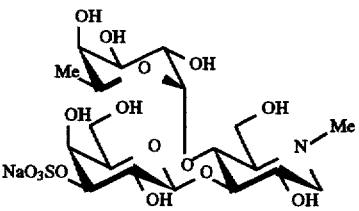

(1) Synthesis of methyl 2,6-di-O-benzoyl-3-O-levuloyl-1-thio-β-D-galactopyranoside In dichloromethane (20 ml)-pyridine (20 ml) was dissolved methyl 2,6-di-O-benzoyl-1-thio-β-D-galactopyranoside (740 mg) followed by addition of 4-dimethylaminopyridine (220 mg, 1 eq). After the mixture was cooled to −50° C., a solution of levulinic anhydride (570 mg, 1.5 eq) in dichloromethane (10 ml) was added dropwise and the mixture was stirred at −50° C. for 20 minutes. After the completion of reaction was confirmed by TLC, the reaction mixture was extracted with dichloromethane and washed with 2N HCl and water. The extract was dehydrated over anhydrous sodium sulfate and filtered and the filtrate and washings were pooled and concentrated under reduced pressure. The residue was subjected to column chromatography (Wakogel C-200, eluent: ethyl acetate-hexane=1:2) to provide the title compound (1; 760 mg, 84%).

Optical rotation $[\alpha]_D$ +28.61° (c=0.982, dichloromethane)
Elemental analysis for $C_{26}H_{28}O_5S$ [mol. wt. 516.57]
Calcd. (%): C, 60.45; H, 5.46; N, 0.00 Found (%): C, 60.33; H, 5.28; N, 0.00

(2) Synthesis of methyl 2,4,6-tri-O-benzoyl-3-O-levuloyl-1-thio-β-D-galactopyranoside In pyridine (30 ml) was dissolved the above compound (1; 760 mg) followed by addition of benzoyl chloride (0.2 ml, 1.2 eq) and the mixture was stirred at room temperature overnight. After the completion of reaction was confirmed by TLC, the reaction mixture was extracted with dichloromethane and the extract was washed with 2N HCl and water. The organic layer was dehydrated over anhydrous sodium sulfate and filtered. The filtrate and washings were pooled and concentrated under reduced pressure. The residue was subjected to column chromatography (Wakogel C-200, eluent: ethyl acetate-hexane=1:4) to provide the title compound (2; 760 mg, 84%).

Optical rotation $[\alpha]_D$ +49.72° (c=0.736, dichloromethane)
Elemental analysis for $C_{33}H_{32}O_{10}S$ [mol. wt. 620.68]
Calcd. (%): C, 63.86; H, 5.20; N, 0.00 Found (%): C, 63.85; H, 5.04; N, 0.00

(3) Synthesis of O-(2,4,6-tri-O-benzoyl-3-O-levuloyl-β-D-galactopyranosyl)-(1→3)-2-O-acetyl-4,6-O-benzylidene-N-benzyloxycarbonyl-1,5-dideoxy-1,5-imino-D-glucitol 2-O-acetyl-4,6-O-benzylidene-N-benzyloxycarbonyl-1,5-dideoxy-1,5-imino-D-glucitol (53 mg) and methyl 2,4,6-tri-O-benzoyl-3-O-levuloyl-1-thio-β-D-galactopyranoside (92 mg, 1.2 eq) were dissolved in dichloromethane (4 ml). To this solution was added the desiccant molecular sieves 4A (200 mg) and the mixture was stirred at room temperature overnight. After this mixture was cooled to 0° C., N-iodosuccinimide (67 mg, 2.4 eq) and trimethylsilyl trifluoromethanesulfonate (6 μl, 0.24 eq) were added and the mixture was stirred at 0° C.-room temperature overnight. After the completion of reaction was confirmed by TLC, the molecular sieves were filtered off and the filtrate was extracted with dichloromethane and washed with sodium carbonate solution, sodium thiosulfate solution, and water. The extract was dehydrated over anhydrous sodium sulfate and filtered and the filtrate and washings were pooled and concentrated under reduced pressure. The residue was subjected to column chromatography (Wakogel C-200, eluent: dichloromethane-methanol=500:1) to provide the title compound (3; 108 mg, 87%).

Optical rotation $[\alpha]_D$ −14.43° (c=2.166, dichloromethane)
Elemental analysis for $C_{55}H_{53}NO_{17}$ [mol. wt. 1000.02]
Calcd. (%): C, 66.06; H, 5.34; N, 1.40 Found (%): C, 65.93; H, 5.11; N, 1.37

(4) Synthesis of O-(2,4,6-tri-O-benzoyl-3-O-levuloyl-β-D-galactopyranosyl)-(1→3)-2-O-acetyl-N-benzyloxycarbonyl-1,5-dideoxy-1,5-imino-D-glucitol In 80% acetic acid-water (20 ml) was dissolved the above compound (3; 323 mg) and the solution was stirred at 45° C. overnight. After the completion of reaction was confirmed by TLC, the reaction mixture was concentrated and the residue was subjected to column chromatography (Wakogel C-200, eluent: dichloromethane-methanol=125:1) to provide the title compound (4; 252 mg, 86%).

Optical rotation $[\alpha]_D$ −39.32° (c=0.656, dichloromethane)
Elemental analysis for $C_{48}H_{49}NO_{17}$ [mol. wt. 911.91]
Calcd. (%): C, 63.22; H, 5.42; N, 1.54 Found (%): C, 62.92; H, 5.17; N, 1.28

(5) Synthesis of O-(2,4,6-tri-O-benzoyl-3-O-levuloyl-β-D-galactopyranosyl)-(1→3)-2-O-acetyl-6-O-tert-butyldimethylsilyl-N-benzyloxycarbonyl-1,5-dideoxy-1,5-imino-D-glucitol In dichloromethane (10 ml)-pyridine (5 ml) was dissolved the above compound (4; 213 mg). After the solution was cooled to 0° C., tert-butyldimethylsilyl chloride (176 ml, 3 eq) was added and the mixture was stirred at room temperature overnight. After the completion of reaction was confirmed by TLC, the reaction mixture was extracted with dichloromethane and washed with 2N HCl and water. The extract was dehydrated over anhydrous sodium sulfate and filtered and the filtrate and washings were pooled and concentrated under reduced pressure. The residue was subjected to column chromatography (Wakogel C-200, eluent: dichloromethane-methanol=250:1) to provide the title compound (5; 221 mg, 92%).

Optical rotation $[\alpha]_D$ +34.62° (c=1.658, dichloromethane)
Elemental analysis for $C_{54}H_{63}NO_{17}Si$ [mol. wt. 1026.17]
Calcd. (%): C, 63.21; H, 6.19; N, 1.36 Found (%): C, 63.17; H, 6.00; N, 1.21

(6) Synthesis of O-(2,4,6-tri-O-benzoyl-3-O-levuloyl-β-D-galactopyranosyl)-(1→3)-O-[(2,3,4-tri-O-benzyl-α-L-fucopyranosyl)-(1→4)]-2-O-acetyl-6-O-tert-butyldimethylsilyl-N-benzyloxycarbonyl-1,5-dideoxy-1,5-imino-D-glucitol The above compound (5; 47 mg) and methyl 2,3,4-tri-O-benzyl-1-thio-β-L-fucopyranoside (26 mg, 1.2 eq) were dissolved in benzene (5 ml). To this solution was added the desiccant molecular sieves 4A (100 mg) and the mixture was stirred at room temperature overnight. Then, dimethyl (methylthio)sulfonium triflate (63 mg, 4 eq) was added at 7° C. and the mixture was stirred at 7° C. for 1.5 hours. After the completion of reaction was confirmed by TLC, methanol (1 ml) and triethylamine (40 ml) were added at 0° C. and the molecular sieves were filtered off. The filtrate and washings were pooled and concentrated under reduced pressure and the residue was extracted with dichloromethane and washed with sodium carbonate and water. The extract was dehydrated over anhydrous sodium sulfate and filtered and the filtrate and washings were pooled and concentrated under reduced pressure. The residue was subjected to column chromatography (Wakogel C-200, eluent: ethyl acetate-hexane=1:2) to provide the title compound (6; 36 mg, 55%).

Optical rotation $[\alpha]_D$ −43.03° (c=0.488, dichloromethane)
Elemental analysis for $C_{81}H_{91}NO_{21}Si$ [mol. wt. 1442.69]
Calcd. (%): C, 67.44; H, 6.36; N, 0.97 Found (%): C, 67.25; H, 6.19; N, 0.72

(7) Synthesis of O-(2,4,6-tri-O-benzoyl-3-O-levuloyl-β-D-galactopyranosyl)-(1→3)-O-[(2,3,4-tri-O-benzyl-α-L-fucopyranosyl)-(1→4)]-2-O-acetyl-N-benzyloxycarbonyl-1,5-dideoxy-1,5-imino-D-glucitol The above compound (6; 36 mg) was dissolved in 80% acetic acid-water (10 ml) and the solution was stirred at room temperature for 3 hours. After the completion of reaction was confirmed by TLC, the reaction mixture was concentrated under reduced pressure and the residue was subjected to column chromatography (Wakogel C-200, eluent: dichloromethane-methanol=125:1) to provide the title compound (7; 29 mg, 88%).

Optical rotation $[\alpha]_D$ −42.88° (c=0.988, dichloromethane)
Elemental analysis for $C_{75}H_{77}NO_{21}$ [mol. wt. 1328.43]
Calcd. (%): C, 67.81; H, 5.84; N, 1.05 Found (%): C, 67.71; H, 5.77; N, 0.97

(8) Synthesis of O-(2,4,6-tri-O-benzoyl-3-O-levuloyl-β-D-galactopyranosyl)-(1→3)-O-[(2,3,4-tri-O-benzyl-α-L-fucopyranosyl)-(1→4)]-2-O-acetyl-6-O-benzoyl-N-benzyloxycarbonyl-1,5-dideoxy-1,5-imino-D-glucitol The above compound (7; 29 mg) was dissolved in pyridine (10 ml) followed by addition of benzoyl chloride (3 μl, 1.2 eq) and the mixture was stirred at room temperature overnight. After the completion of reaction was confirmed by TLC, the reaction mixture was extracted with dichloromethane and the extract was washed with 2N HCl and water. The extract was dehydrated over anhydrous sodium sulfate and filtered. The filtrate and washings were pooled and concentrated under reduced pressure and the residue was subjected to column chromatography (Wakogel C-200, eluent: dichloromethane-methanol=250:1) to provide the title compound (8; 31 mg, quantitative).

Optical rotation $[\alpha]_D$ -60.18° (c=2.366, dichloromethane)
Elemental analysis for $C_{82}H_{81}NO_{22}$ [mol. wt. 1432.54] Calcd. (%): C, 68.75; H, 5.70; N, 0.98 Found (%): C, 68.48; H, 5.42; N, 0.70

(9) Synthesis of O-(2,4,6-tri-O-benzoyl-β-D-galactopyranosyl)-(1→3)-O-[(2,3,4-tri-O-benzyl-α-L-fucopyranosyl)-(1→4)]-2-O-acetyl-6-O-benzoyl-N-benzyloxycarbonyl-1,5-dideoxy-1,5-imino-D-glucitol In ethanol (10 ml) was dissolved the above compound (8; 31 mg) followed by addition of hydrazine acetate (2 mg, 1.2 eq) and the mixture was stirred at room temperature for 1 hour. After the completion of reaction was confirmed by TLC, the reaction mixture was concentrated under reduced pressure and the residue was subjected to column chromatography (Wakogel C-200, eluent: dichloromethane-methanol=125:1) to provide the title compound (9; 27 mg, 93%).

Optical rotation $[\alpha]_D$ -75.74° (c=2.020, dichloromethane)
Elemental analysis for $C_{77}H_{75}NO_{20}$ [mol. wt. 1334.43] Calcd. C, 69.31; H, 5.67; N, 1.05 Found C, 69.09; H, 5.41; N, 0.82

(10) Synthesis of O-(2,4,6-tri-O-benzoyl-3-O-sulfo-β-D-galactopyranosyl)-(1→3)-O-[(2,3,4-tri-O-benzyl-α-L-fucopyranosyl)-(1→4)]-2-O-acetyl-6-O-benzoyl-N-benzyloxycarbonyl-1,5-dideoxy-1,5-imino-D-glucitol In N,N-dimethylformamide (0.5 ml) was dissolved the above compound (9; 101 mg) followed by addition of pyridine-sulfur trioxide complex (96 mg, 1.2 eq) and the mixture was stirred at room temperature for 2 hours. After the completion of reaction was confirmed by TLC, methanol (1 ml) was added at 0° C. and the mixture was stirred for 30 minutes. This reaction mixture was concentrated under reduced pressure and the residue was subjected to column chromatography (Wakogel C-200, eluent: dichloromethane-methanol=15:1) to provide the title compound (10; 109 mg, quantitative).

Optical rotation $[\alpha]_D$ -55.56° (c=2.012, dichloromethane)
Elemental analysis for $C_{77}H_{75}NO_{23}S$ [mol. wt. 1414.50] Calcd. (%): C, 65.38; H, 5.34; N, 0.99 Found (%): C, 65.32; H, 5.21; N, 0.98

(11) Synthesis of O-(2,4,6-tri-O-benzoyl-3-O-sulfo-β-D-galactopyranosyl)-(1→3)-O-[(α-L-fucopyranosyl)-(1→4)]-2-O-acetyl-6-O-benzoyl-1,5-dideoxy-1,5-imino-N-methyl-D-glucitol sodium salt The above compound (10; 99 mg) was treated with the ion exchange resin Dowex-Na$^+$ and dissolved in methanol (5 ml). Then, formalin (0.5 ml) and palladium chloride (200 mg) subjected to catalytic hydrogenation and washed with methanol beforehand was added. The mixture was subjected to catalytic hydrogenation reaction at room temperature with stirring for 4 days. After the completion of reaction was confirmed by TLC, the palladium was filtered off and washed with methanol. The filtrate and washings were pooled and concentrated under reduced pressure and the residue was subjected to column chromatography (Wakogel C-200, eluent: dichloromethane-methanol=10:1) to provide the title compound (11; 66 mg, 92%).

Optical rotation $[\alpha]_D$ -30.49° (c=0.892, methanol)
Elemental analysis for $C_{49}H_{52}NO_{21}SNa$ [mol. wt. 1046.00] Calcd. (%): C, 56.27; H, 5.01; N, 1.34 Found (%): C, 56.15; H, 4.98; N, 1.24

(12) Synthesis of O-(3-O-sulfo-β-D-galactopyranosyl)-(1→3)-O-[(α-L-fucopyranosyl)-(1→4)]-1,5-dideoxy-1,5-imino-N-methyl-D-glucitol sodium salt The above compound (11; 56 mg) was dissolved in methanol (5 ml) followed by addition of sodium methoxide until the pH became 12. The mixture was then stirred at room temperature for 2 days. After the completion of reaction was confirmed by TLC, the reaction mixture was concentrated under reduced pressure and the residue was subjected to gel filtration (Sephadex LH-20, eluent: methanol-water=1:1) to provide the title compound (12; 31 mg, quantitative).

Optical rotation $[\alpha]_D$ -56.14° (c=0.114, methanol-water=1:1)

Elemental analysis for $C_{19}H_{34}NO_{16}SNa$ [mol. wt. 587.53] Calcd. (%): C, 38.84; H, 5.83; N, 2.38 Found. (%): C, 38.73; H, 5.74; N, 2.14

[Test Example]
Protocol for E-selectin-dependent HL60/HUVEC adhesion test 5-th passage human vascular endothelial cells (HUVEC), harvested and subcultured serially in the routine manner, were seeded in a 1% gelatin-coated 96-well culture plate at $2\times10^4$ cells/well. The cells were cultured in a $CO_2$ incubator at 37° C. overnight and the cell layer was washed with 100 μl of RPMI/FCS/HEPES medium (RPMMI-1640, 10% FCS, 25 mM HEPES, pH 7.4) twice. Then, 100 μl of RPMI/FCS/HEPES containing 100 U/ml of IL-1β was added and the incubation was carried out for 4 hours (activation). To assess cell adhesion to non-activated cells, wells supplied with RPMI/FCS/HEPES only were also provided (basal).

Cultured human leukemia cells (HL60) were washed with FCS-free RPMI-1640 (RPMI/HEPES) twice and suspended in 10 ml of 0.5% glutaraldehyde-containing RPMI/HEPES, followed by 20 minutes of fixation on ice. After fixation, the cells were washed with RPMI/HEPES 3 times and adjusted to $2\times10^6$ cells/ml by dilution with RPMI/FCS/HEPES, the cells were stored on ice until use.

After the activation, HUVECs were washed with 100 μl of RPMI/FCS/HEPES 3 times, 50 μl of RPMI/FCS/HEPES (control) or 50 μl of a solution of the compound in RPMI/FCS/HEPES (300 μg/ml) was added and the plate was incubated at room temperature for 30 minutes. Then, 50 μl of HL60 cells ($1\times10^5$ cells/well) were added into the wells and the plate was incubated at 37° C. for 45 minutes. The wells were filled with RPMI/FCS/HEPES and closed up with a microplate seal without air bubbles, the plate was inverted and allowed to leave for 1 hour, thereby, remove the unbound HL60 cells.

Method of Determining the Adherent Cell Count

The number of adherent cells was determined by the measuring of the activity of myeloperoxidase (MPO), an intracellular enzyme of EL60 cells. Thus, 50 μl of phosphate buffer (50 mM, pH 6.0) containing 0.5% hexadecyltrimethylammonium bromide (HTAB) was added to each well and the plate was incubated at room temperature for 30 minutes to solubilize MPO from the cells. At the same time, as the standard, a known number of similarly treated HL60 cells was provided in one row of the 96-well plate. Then, 200 μl of phosphate buffer (100 mM, pH 5.4) containing 0.6 mM dianisidine dihydrochloride and 0.4 mM $H_2O_2$ was added and the reaction was carried out at room temperature for 20 minutes. The absorbance at 450 nm was measured with Bio-Rad Model 3550 microplate reader. The adherent cell count was determined against a calibration curve constructed from the absorbance determined with the cells used as standard. The experiment was performed using 6 wells per treatment. From the adherent cell count in each well, the cell adhesion rate for each treatment was calculated with the control count being taken as 100%, and the mean ± standard error for 6 wells were calculated. The results are shown in Table 1.

TABLE 1

|  | Cell adhesion rate |
| --- | --- |
| Control | 100.0 ± 3.4 |
| Basal | 12.0 ± 0.6* |
| Compound of Example 2 | 77.0 ± 2.0* |

*P < 0.01, vs. control

[Results]

The results of the above experiment are presented in Table 1. The compound of Example 2 inhibited cell adhesion by 23% (P<0.01). Thus, the compounds of the invention have high cell adhesion-inhibitory activity. The above results indicate that the compounds of the present invention are of value as a drug for the prevention and treatment of diseases which are etiologically associated with cell adhesion, such as inflammations, immune diseases, and viral infections.

What is claimed is:

1. A moranoline derivative of the following general formula I:

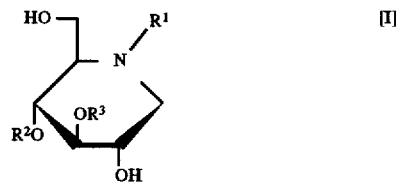

wherein $R^1$ represents hydrogen or lower alkyl; $R^2$ and $R^3$ are dissimilar and each represents galactopyranosyl or fucopyranosyl, which is substituted by hydroxysulfonyl or a metal salt thereof.

2. The moranoline derivative according to claim 1 wherein the metal salt of hydroxysulfonyl is an alkali metal salt or an alkaline earth metal salt.

3. The moranoline derivative according to claim 1 wherein $R^2$ represents galactopyranosyl substituted by sodium hydroxysulfonyl and $R^3$ represents fucopyranosyl.

4. The moranoline derivative according to claim 1 wherein $R^2$ represents fucopyranosyl and $R^3$ represents galactopyranosyl substituted by sodium hydroxysulfonyl.

* * * * *